United States Patent
Reddy (10) Patent No.: US 6,499,476 B1
(45) Date of Patent: Dec. 31, 2002

(54) VAPOR PRESSURE DETERMINATION USING GALVANIC OXYGEN METER

(75) Inventor: Sam Raghuma Reddy, West Bloomfield, MI (US)

(73) Assignee: General Motors Corporation, Detroit, MI (US)

( * ) Notice: Subject to any disclaimer, the term of this patent is extended or adjusted under 35 U.S.C. 154(b) by 15 days.

(21) Appl. No.: 09/709,882

(22) Filed: Nov. 13, 2000

(51) Int. Cl.$^7$ ............................................... F02D 41/00
(52) U.S. Cl. ........................................ 123/704; 123/520
(58) Field of Search ................................ 123/704, 520, 123/519, 518, 516

(56) References Cited

U.S. PATENT DOCUMENTS

| | | | | |
|---|---|---|---|---|
| 4,209,378 A | * | 6/1980 | Schinohara et al. ..... | 204/195 S |
| 5,054,460 A | | 10/1991 | Ogita .......................... | 123/571 |
| 5,111,796 A | | 5/1992 | Ogita .......................... | 123/520 |
| 5,363,832 A | * | 11/1994 | Suzumura et al. .......... | 123/704 |
| 5,823,171 A | * | 10/1998 | Farmer et al. ............... | 123/704 |
| 5,884,610 A | | 3/1999 | Reddy ........................ | 123/520 |
| 5,977,525 A | * | 11/1999 | Sahashi ...................... | 219/494 |
| 6,237,575 B1 | * | 5/2001 | Lampert et al. ............ | 123/520 |

* cited by examiner

Primary Examiner—Tony M. Argenbright
Assistant Examiner—Mahmoud Gimie
(74) Attorney, Agent, or Firm—Kathryn A. Marra (57) ABSTRACT

A method and apparatus for galvanically measuring vapor pressure of a volatile liquid is described. Vapor pressure of the volatile liquid is derived by galvanically detecting the reduction in oxygen partial pressure in air that is caused by evaporation of the volatile liquid into that air. In one example, an automotive engine/fuel EVAP system is described in which fuel vapor pressure exiting an EVAP canister is measured during purging. The measurement is used to compensate the primary fuel supply to better control overall air/fuel ratio to the engine during purging. In another example, a galvanic oxygen meter is used to identify the type of volatile liquid, including the RVP of engine fuel.

17 Claims, 3 Drawing Sheets

VAPOR PRESSURE DETERMINATION USING GALVANIC OXYGEN METER

TECHNICAL FIELD

This invention relates to vapor pressure detection and diagnostics. Most specifically, the invention relates to detection of gasoline vapor pressure and its application to fuel control in an internal combustion engine.

BACKGROUND OF THE INVENTION

There are instances where one wants to know the vapor pressure of a volatile liquid for control and/or diagnostic purposes, but direct and/or immediate vapor pressure measurement is not practical by ordinary techniques. In addition, one might want to know the vapor pressure of the liquid as it actually exists under the conditions of its storage container. In one example, one may simply want to quickly identify the type of fuel contained in an automobile fuel tank or in a bulk storage tank. Another example involves automotive internal combustion engine control systems. Precise and immediate knowledge of fuel vapor pressure, i.e., fuel volatility, is often desired in automotive engine control systems. For fuel control of an automobile internal combustion engine, fuel volatility is generally measured as reid vapor pressure (RVP), which is vapor pressure measured at 100° F. under a specified manner of measurement. High gasoline RVP improves engine startability and driveability at low ambient temperatures but can have a negative effect on precision of certain fueling system diagnostics. It is recognized that vapor pressure, and more specifically RVP, can vary significantly among available fuels. Hence, it is desirable that the fuel control system be able to identify the type of fuel being used and, more specifically, vapor pressure of the fuel being used. As pointed out in my earlier U.S. Pat. No. 5,884,610 Reddy, it is desirable to determine the precise vapor pressure, usually as RVP, of the fuel being used by an automobile's internal combustion engine. It is desired so that the fueling system control and diagnostics can be adjusted to match it. This provides increased emission control, driveability and integrity of diagnostics.

However, just knowing the RVP of the fuel being furnished to an engine is not enough information to adequately control the ratio of air and fuel being supplied to the engine if the engine has an EVAP system. Most United States automobiles have on-board EVAP systems that include a canister for collecting and storing fuel vapors evaporating from the engine fuel tank. The canister is purged of these vapors by allowing air to enter the storage canister upstream from a canister outlet to create an air/fuel mixture of unknown air to fuel ratio. The canister air/fuel mixture is drawn into the engine for combustion during engine operation, while the engine is already running under a primary air and fuel control. Accordingly, the air/fuel mixture coming to the engine from the canister supplements the engine's primary air/fuel feed. In other words, it adds fuel and air to the primary air/fuel feed. However, before purge of the canister starts, the primary air/fuel mixture being fed to the engine is already balanced to a predetermined optimum. Introducing the purge vapors to it will upset this balance.

The volume of air/fuel mixture exiting the canister is substantially fixed. However, the ratio of air to fuel in the mixture is not. To provide more precise fuel control for the engine, it is desirable to know the air to fuel ratio of the mixture as it exits the canister, and then concurrently adjust the primary fuel control to compensate for it. The primary fuel control can then add or reduce its primary fuel supply so that the total resultant air/fuel mixture combusted in the engine is at the desired level even during canister purge. This is a forward-looking method of fuel control, as compared to a reactive fuel control in which fuel is controlled in response to a signal from an exhaust gas oxygen sensor.

I recognize that vapor pressure of the fuel in the mixture exiting the canister is a measure of mixture air/fuel ratio. If fuel vapor pressure in the exiting mixture is measured during purge, a more forward control of engine air/fuel ratio can be obtained. As indicated above, knowing the vapor pressure, i.e., concentration, of the fuel in the air coming from the canister allows one to concurrently adjust the primary air/fuel feed a corresponding amount. One does not have to wait for feedback from the exhaust oxygen sensor to adjust the primary air/fuel feed. Accordingly, this provides a forward control of air/fuel ratio to the engine that offers a variety of benefits.

EVAP systems, also referred to herein as systems, include on-board refueling vapor recovery (ORVR) systems. These systems may include a vapor line from an automobile fuel tank to a canister filled with fuel-adsorbing material, usually carbon. They also include a valved vapor line from the canister to the intake manifold of the internal combustion engine of the automobile. During refueling of the automobile fuel tank, fuel vapors in the fuel tank pass through the fuel tank vapor line to the canister, where they are trapped. The vapor line not only reduces ambient emission of fuel tank vapors from refueling but also during subsequent oration of fuel in the tank. The fuel vapors trapped in the canister are purged from the adsorbing material from time to time during engine operation, for consumption by the engine along with the engine's primary source of fuel. The fuel, i.e., hydrocarbons, in the purge vapor can become a significant source of fuel fed to the engine. It is, therefore, important to know the hydrocarbon concentration in the purge vapor to obtain better control of fuel introduced into the engine.

In the past, some ORVR systems included complex on-board means for determining fuel vapor pressure. U.S. Pat. No. 5,054,460 Ogita and U.S. Pat. No. 5,111,796 Ogita each describe measuring vapor pressure of automobile fuel by placing a rotary vaned sensor in a vapor line from the automobile fuel tank to an EVAP canister. Fuel vapors passing along the line rotate the sensor, which emits electrical pulses indicating rate of rotation. The Ogita sensor only gives a broad indication of vapor pressure in the tank. It does not indicate what the fuel vapor pressure, especially RVP, is in the purge vapors from the EVAP canister.

In my earlier U.S. Pat. No. 5,884,610 Reddy, I determine RVP of the fuel vapor pressure in the purge vapors rather precisely, using an estimating technique. In my U.S. Pat. No. 5,884,610 Reddy, I describe an engine control system that remembers engine performance under given control conditions immediately before the purge valve on the EVAP canister is opened. That performance is then compared to engine performance immediately after the purge valve is opened. Based on the difference in engine performance, a valuable estimate of fuel vapor pressure is made. Based on this estimate, a signal is fed back to the primary air/fuel ratio control system to appropriate it adjust it for maintaining optimum air/fuel delivery to the engine. However, the system operates after purge starts, by observing its effect on engine performance estimating what is in the purge vapors, and then issuing an estimated adjustment signal to the primary fuel control.

I have now discovered a technique by which fuel vapor pressure can be directly measured, not just estimated. In some instances, such as EVAP systems, the measurement can be done in the EVAP canister itself or in the vapor line from the EVAP canister to the engine. This allows one to not only know fuel vapor pressure in the fuel tank but also to know the fuel vapor pressure, i.e., concentration, of fuel in EVAP canister purge vapors. In other systems, measurement might be in an automobile fuel tank or other fuel storage tank. The measurement is direct, not estimated.

Still further, this invention is also useful for diagnostic identification of fuel in an automobile by the primary fuel delivery system or by a service technician working on a fuel problem. This invention can also be used to quickly identify fuel volatility in other forms of storage and shipping tanks. This can be a significant help to shippers in confirming identity on site of what they think should be in a storage or transfer container. Still further, this invention need not be limited to measurement of fuel vapor pressure. Vapor pressure of various other volatile liquids could be analogously measured as well.

SUMMARY OF THE INVENTION

The object of the present invention is to provide an accurate measurement of the vapor pressure of a volatile liquid by galvanically measuring oxygen concentration in a mixture of air and vapors of that liquid. The measurement is made by simply exposing an ordinary oxygen sensor to a mixture of air and vapors of the liquid at atmospheric pressure. The sensor provides an output voltage that is a measure of oxygen partial pressure in the air/vapor mixture. The oxygen to nitrogen ratio in air is a constant, of about 1 to 4. Multiplying the oxygen partial pressure by that constant (i.e., about 5) is an effective measure of air partial pressure in the mixture. Subtracting the air partial pressure from atmospheric pressure provides a measure of fuel vapor partial pressure.

For applications where more accuracy is desired, such as automotive fuel control applications, it may be desirable to concurrently also measure temperature, and perhaps even atmospheric pressure. For many applications, fuel vapor pressure can be adequately characterized by considering that atmospheric pressure is a fixed quantity, such as a fixed reference voltage, representing a standard pressure of 760 mm of mercury or 14.7 pounds per square inch at room temperature. However, if a more precise determination is desired, atmospheric pressure can actually be measured and then used as the comparison quantity. Compensation can be made electrically for deviation in measuring temperature from the reference room temperature. If desired, the fuel vapor pressure measured by my oxygen meter can be converted to reid vapor pressure (RVP) according to the following formula:

$$RVP = 1/(A*T) EXP(\ln P_g + 2731.41/T) \quad (1)$$

where: A is 21.51

B is 2731.41

$P_g$ is vapor pressure of fuel in pounds per square inch at the measuring temperature T T is the $P_g$ measuring temperature in degrees Kelvin Hence, measurement of vapor pressure by my technique is readily usable in various vapor pressure units or forms, as might be desired.

BRIEF DESCRIPTION OF THE DRAWINGS

The foregoing and other objects of this invention are best understood in light of the following description and by reference to the drawings in which.

DESCRIPTION OF THE PREFERRED EMBODIMENT

As indicated above, this invention can be used in connection with an automobile EVAP system. Such systems are well known and are amply described in the prior art. One such system is referred to as an on-board refueling vapor recovery (ORVR) system and is described in detail in my earlier U.S. Pat. No. 5,884,610 Reddy, which is incorporated herein by reference. Significant aspects of an EVAP system shall hereinafter be more fully described. For simplicity, this invention shall first be described in connection with those parts of an automobile EVAP system that include a fuel tank 10, EVAP canister 12, the automobile engine 14, and their interconnecting hardware, making reference to FIGS. 1 and 2.

Figure 1:
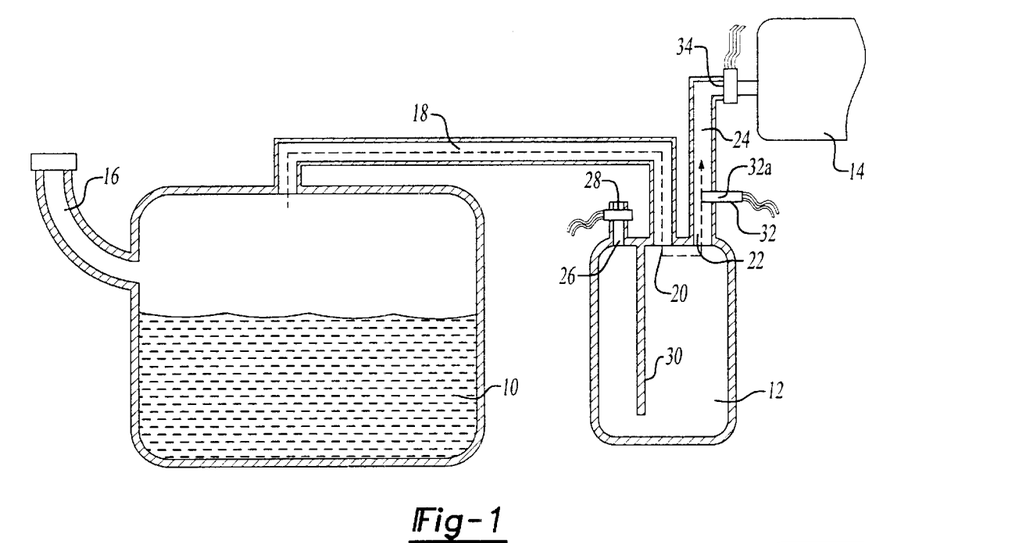
FIG. 1 is a schematic diagram of relevant parts of an automobile fuel vapor emission control system that incorporates an oxygen sensor in the purge vapor outlet of an EVAP canister, a purge valve on that outlet, and an air inlet valve to the canister. In this view, the purge valve is open and the air inlet valve is closed.
Figure 2:
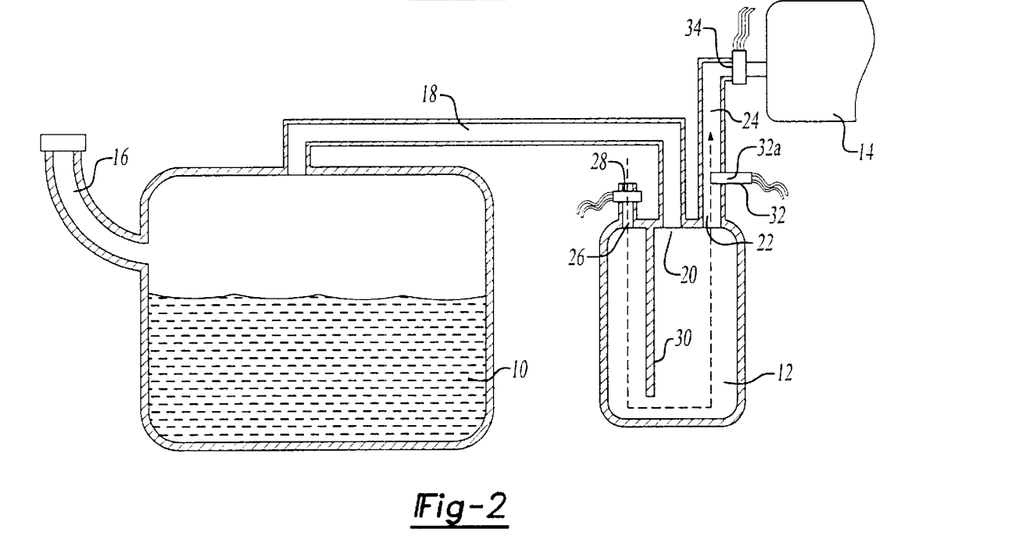
FIG. 2 is a schematic diagram of the same automobile EVAP system portions shown in FIG. 1 but differs in this view by representing that both the purge valve and the air inlet valve on the EVAP canister are open.

FIGS. 1 and 2 show the fuel tank 10 as having a filler spout 16. Filler spout 16 provides access to the tank for re-filling the tank when needed. Filler spout 16 provides access of ambient air to the tank while the tank is being fueled. Air flow into tank 10 can also occur through the EVAP canister 12 since the EVAP canister air vent valve 28 would normally be open, except for fuel tank diagnostics, including tank fuel vapor pressure determinations by my galvanic oxygen meter. Other and more direct air vents to the tank might also be provided, so long as they do not interfere with purging of the EVAP canister 12.

Fuel that evaporates in tank 10 passes from tank 10 to an EVAP canister 12 through vapor conduit line 18. As indicated above, the EVAP canister is filled with a fuel adsorptive material (not shown) of any convenient type, as, for example, activated carbon. EVAP canister 12 has an inlet opening 20 to vapor line 18 and an outlet opening 22 to a vapor line 24. EVAP canister 12 also has an ambient air inlet 26, whose opening and closing to ambient air is controlled by valve 28. Ambient air inlet opening 26 can be of about the same diameter as the vapor inlet and outlets 20 and 22. Air vent valve 28 would be normally open except for temporary closures for diagnostic or other such purposes, which is illustrated in FIG. 1. It should be noted that inside EVAP canister 12 ambient air inlet 26 is separated from vapor inlet 20 and vapor outlet 22 by an internal baffle 30. It is also to be noted baffle 30 does not separate vapor inlet 20 from vapor outlet 22. Hence, there is a direct communication between fuel vapor in tank 10 and galvanic oxygen meter 32 in vapor line 24.

Vapor line 24 extends from outlet 22 of EVAP canister 12 to engine 14. More specifically, and as can be seen from FIG. 4, vapor line 24 extends to the intake manifold of engine 14. Vapor line 24 contains a purge valve 34 that, when closed, blocks communication between EVAP canister 12 and engine 14. Canister vent valve 28 remains normally open and purge valve 34 is pulse width modulated open for canister purging. The canister is continuously purged most of the time when the engine is running. It can also be seen that the sensing tip 32a of a galvanic oxygen meter 32 is disposed in the exit line 24 from canister 12. Accordingly, when engine 14 is running and purge valve 34 is open, sensor tip 32a is exposed to fuel vapors that were previously adsorbed in EVAP canister 12, and to any fuel vapors concurrently evaporating from fuel tank 10. Sensing tip 32a can be threaded into a fitting on vapor line 24. Sensing tip 32a is preferably attached to vapor line 24 adjacent outlet 22 of EVAP canister 12, as shown in FIGS. 1 and 2. However, if desired, it could be attached directly to the wall of EVAP canister 12, preferably threaded into the top of the EVAP canister 12, adjacent the outlet opening 22.

FIG. 1 shows the system in condition for RVP detection of the fuel in tank 10. Engine 14 is running. Air vent valve 28 is closed and purge valve 34 is open. Vapor in headspace of tank 10 is thus exposed to engine intake manifold vacuum and is drawn into contact with oxygen meter 32. Meter 32 detects hydrocarbon concentration in the vapor as vapor pressure, and can report it as voltage for use by an engine controller, such as controller 54 in FIG. 4. If desired, meter 32 and/or the controller could include means to convert the vapor pressure reading to reid vapor pressure (RVP). It is recognized that the RVP or fuel type determination could be made simpler and perhaps a little more precise by installing a second galvanic oxygen meter 32 in the headspace of tank 10. However, this adds other obvious costs and complexities that I prefer to avoid. I believe that the better tradeoff is to use one meter, add an air vent valve to the EVAP canister, and control the valves as indicated in FIGS. 1 and 2.

In FIG. 1, with purge valve 34 open and vent valve 28 closed, the tank fuel vapors are drawn directly to oxygen meter 32 through lines 18 and 24. More specifically, fuel evaporating from fuel tank 10 mixes with atmospheric pressure air in fuel tank 10 to form a gaseous mixture. The gaseous mixture passes through vapor line 18 and EVAP canister openings 20 and 22 into vapor line 24, where it contacts the sensor tip 32a of oxygen meter 32. The air portion of the gaseous mixture contains a fixed ratio of oxygen to nitrogen of about 1 to 4. More specifically, air contains 20.9% oxygen by volume and the balance mostly nitrogen. The fuel vapors, being a gas, exert a partial pressure along with air in the gaseous mixture. According to Dalton's Law, the oxygen, nitrogen and fuel vapors each exert their own partial pressure in the mixture.

Since the gaseous mixture in the headspace of tank 10 is at atmospheric pressure, the partial pressure of air in the mixture will be lower than atmospheric pressure. It will be reduced by whatever partial pressure the fuel vapors represent. In other words, the partial pressures of oxygen and nitrogen in the mixture will both be reduced, in a fixed ratio to one another, in an amount determined by the partial pressure exerted by the fuel vapors.

Accordingly, in this invention, I measure the oxygen partial pressure in air/fuel mixture and multiply it by the oxygen to nitrogen proportionality. I then compare that pressure to atmospheric pressure to determine how much air partial pressure in the mixture is reduced. That reduction equals the partial pressure of the fuel vapors in the mixture. In other words, vapor pressure of the fuel in the air/fuel mixture is obtained by subtracting the reduced air partial pressure in the mixture from atmospheric pressure. In actual measurement, oxygen meter 32 might have sensing tip 32a compare its voltage with an ambient air reference voltage to obtain a voltage ratio, and subtract that ratio from one. For other applications, the output could be shown on a meter scale that represents multiples or fractions of atmospheric pressure units. Each unit could represent 14.7 pounds per square inch, 760 mm of mercury, actual atmospheric pressure at the time of measurement, and/or reid vapor pressure units, as might be desired.

As indicated above, in this invention, the oxygen meter 32 can do more than just identify vapor pressure, including RVP, of fuel in tank 10. My meter 32 can also identify the vapor pressure, i.e., fuel proportion, of fuel in purged air/fuel mixtures from an EVAP canister. Because of that capability, I choose to operate an EVAP, or ORVR, system differently from conventional such systems. In conventional EVAP systems, including ORVR systems, fuel vapor is periodically purged from the EVAP canister. However, in my invention, I choose to purge the EVAP canister almost all the time the engine is running. The reason I can do this is that I can substantially continuously monitor and identify the air/fuel ratio in the air stream exiting the EVAP canister and entering the engine intake. Since I know the supplemental air/fuel ratio, I can concurrently adjust the air/fuel ratio from the primary fuel source to substantially maintain a constant total predetermined air/fuel ratio entering the engine. Thus, air/fuel ratio for the engine is controlled before it is combusted in the engine, instead of controlling it after combustion. In many systems, an oxygen sensor is used to control the engine after engine warm up. The engine is given a predetermined air/fuel ratio for engine warm up. After warm up, the exhaust gas oxygen sensor provides a signal to the engine control computer for determining air/fuel ratio from the primary fuel feed system. Essentially, the primary fuel feed system waits for a signal from the exhaust gas oxygen sensor, and then makes an incremental adjustment in air/fuel ratio if an adjustment is needed. The primary fuel feed system then waits for another signal from the exhaust gas oxygen sensor, and makes another incremental adjustment to air/fuel ratio, if needed. This incremental process continues until the proper air/fuel ratio is reached. The exhaust gas oxygen sensor continues to monitor the system for subsequent changes, and may regularly cycle above and below air to fuel stoichiometry. Incremental adjustments of this sort are thus done on a feedback basis. In some systems, the feedback incremental adjustment technique may not be fast enough to adjust the primary fuel feed in response to rapid changes in air/fuel ratio that can occur. One such change is when an EVAP purge valve opens. Other systems may be so slow as to start adjustment on the downslope of any "spike" in air/fuel ratio change. For example, the adjustment to air/fuel ratio may start after the initial surge of canister fuel vapors passes. If so, an air/fuel ratio imbalance occurs twice. It occurs the first time during the start of canister purge, and again after the system tries to correct for initial imbalance but does so too late. It can thus be understood that feedback control can have its limitations. This invention provides immediate identification of and reaction to fuel vapor pressure in the purge vapors. Reaction by the primary fuel feed system can occur forward of the time the exhaust sensor sends a signal. I refer to this new type of air/fuel ratio control as forward control, as compared to feedback control.

FIG. 2 shows that the opening of purge valve 34 provides open communication between EVAP canister 12 and engine 14. Engine intake manifold vacuum draws air into EVAP canister 12 from vent 26, and draws fuel vapors from EVAP canister 12 into engine 14, where they are consumed by engine 14 along with fuel from the engines principal fuel delivery system (not shown). It can be seen that a larger air inlet opening 26 facilitates purge of fuel from the EVAP canister 12. Purge valve 34 can remain open for a fixed period of time, or sensor controls can be used to close it. Because I can identify fuel vapor pressure in the mixture exiting the EVAP canister, I can concurrently adjust primary fuel feed to compensate for it as needed. Accordingly, in my preferred mode of engine operation, purge valve 34 and air vent valve 28 will be open. Fuel vapors from both the EVAP canister 12 and fuel tank 10 will mix and be sensed by sensor tip 32a in vapor line 24. One sensor control for closing purge valve 34 might be a measure of the reduction in purge hydrocarbon concentration below a predetermined value or a measured increase in exhaust gas oxygen above a predetermined value.

In one specific example of this invention, the galvanic oxygen sensor used was Model No. A-01 that was obtained from International Technologies of Germany. It is a commercially-available galvanic type of oxygen sensor. It is designed for use in automotive exhaust gas analyzers for measurement of oxygen concentrations at high temperatures. Such a sensor is reliable, robust, inexpensive, and useful at lower temperatures, too. Any galvanic oxygen sensor that functions at lower temperatures, such as $-40°$ C. up to about $100°$ C. should work. The zirconia oxygen sensor that has been typically used to sense automobile exhaust gas oxygen is not suitable for this application. The zirconia electrolyte is not ionically conductive until it becomes quite hot. Thus, it does not function well, if at all, at the more ordinary temperatures contemplated for this invention.

For completeness of disclosure, construction and operation of a typical galvanic oxygen meter shall be described. A galvanic oxygen meter, such as oxygen meter 32, would include a sensing cathode designed to electrochemically react with oxygen. The meter would also contain a reference anode and an electrolyte that contacts both the cathode and anode. The sensing tip 32a of the oxygen meter would contain the cathode, which would usually be protected by an oxygen-permeable covering or membrane (not shown). Oxygen diffusing through the protective covering or membrane gets electrochemically reduced (i.e., gains electrons) at the cathode. This creates a cathode electrochemical potential. A reactant at the reference electrode creates a reference electrochemical potential. When both the cathode and anode are at atmospheric pressure, the oxygen content of air is acceptable for creating an anode reference voltage. Such a galvanic cell is referred to as a concentration type galvanic cell. By way of example, the zirconia exhaust gas oxygen sensor uses atmospheric oxygen for its reference anode potential. In such a cell, a comparison of the cathode and anode voltages provides an indication of oxygen pressure at the cathode, as compared with atmospheric pressure. If the oxygen at the cathode is part of a gaseous mixture, the voltage comparison gives an indication of oxygen partial pressure in the mixture. If a very precise measure of the oxygen partial pressure is desired, it might be desirable to measure the temperature and pressure at the cathode and anode, and appropriately adjust the measured and reference voltages for temperature and/or pressure differences. This is particularly true if the anode reference voltage does not come from atmospheric oxygen but comes from an internally fixed source of oxygen. This internally fixed source could be an oxygen gas bottle, a mixture of oxides that generate oxygen gas, a metal, etc. For research work, a more sophisticated oxygen meter might include its own source of anode oxygen, temperature sensors and pressure sensors, along with suitable electronics to appropriately adjust cathode and anode voltages to standard temperature and pressure conditions for comparison. However, a simpler version might be quite acceptable for many applications. In such instance, my galvanic oxygen meter might obtain its reference anode potential by simply exposing the sensor's anode to ambient air. In instances where both anode and cathode of the sensor is at ambient pressure and at about the same temperature, a temperature and/or pressure adjustment would be unnecessary for many applications.

As indicated above, some galvanic oxygen sensors have a fixed reference voltage that is independent of ambient, i.e., atmospheric, pressure. If one desires more precise vapor pressure values with such a sensor, compensation for varying cathode ambient pressure changes can be done. For example, many current automobiles include an electronic atmospheric pressure sensor in their engine control systems. The output of the electronic atmospheric pressure sensor could readily be used to adjust oxygen meter output voltage to standard conditions or to reid vapor pressure. It is conceivable that a separate galvanic oxygen meter could even be used to provide an ambient air pressure reference voltage.

As mentioned above, EVAP canister 12 will be maintained at ambient pressure by air vent 26. EVAP canister 12 will stay at about atmospheric pressure even though it has been subject to purging. While the s EVAP canister can get relatively warm under the hood of an automobile, if both electrodes are at about the same temperature, temperature compensation is probably not needed. If ambient air is used to establish the anode reference potential, the anode and cathode gases are then both at atmospheric pressure. In such instance, pressure compensation is not needed. However, for conversion of measured vapor pressure to reid vapor pressure, an accurate measure of the temperature of the fuel vapors at the cathode during measurement is needed. Accordingly, for reid vapor pressure measurements, sensor tip 32a would preferably also include a temperature sensor, such as a thermistor or the like (not shown).

As indicated above, I can measure vapor pressure in other many types of containers, not just EVAP canisters or their exit lines. In many of the other containers, temperature of the oxygen being sensed may not vary widely, as for example in an underground bulk storage tank, or in the hold of fuel tanker ship or barge. In such instance, temperature adjustment would probably be unnecessary. In addition, for accuracy and safety, the cathode of the oxygen meter should not induce any catalytic competing chemical reaction between oxygen and fuel vapors on the cathode surface at the temperature of measurement. More will hereinafter be said about use of my oxygen meter for purposes other than engine control.

Figure 4:
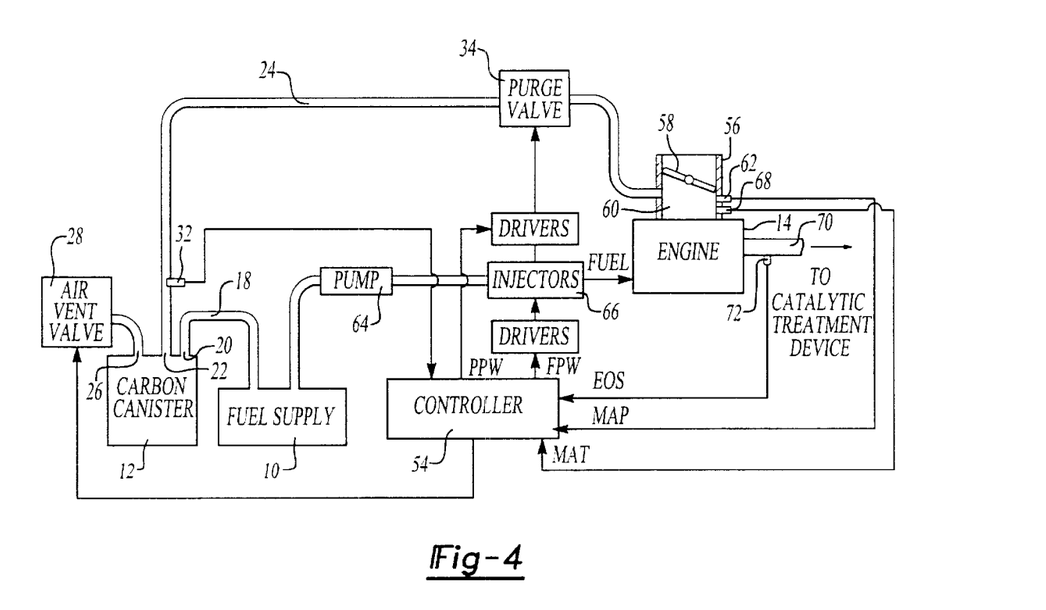
FIG. 4 schematically shows a general diagram of a vehicle fuel and power system, including EVAP system hardware, for carrying out a preferred embodiment of the invention. This figure corresponds to FIG. 1 in my earlier U.S. Pat. No. 5,884,610 Reddy.
Figure 5:
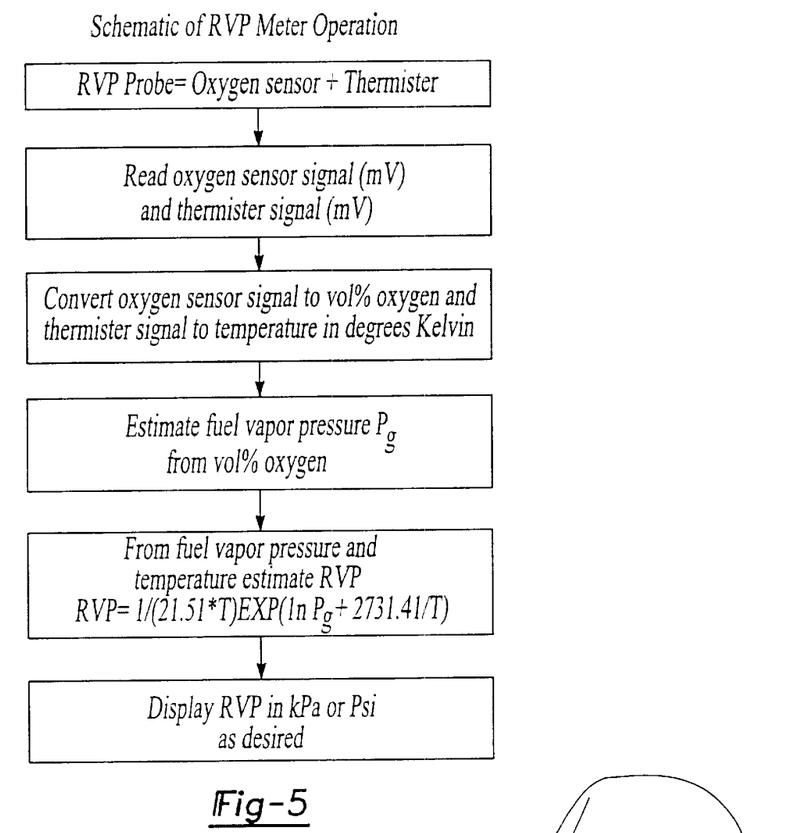
FIG. 5 shows a diagram illustrating steps in the process of my invention.
Figure 6:
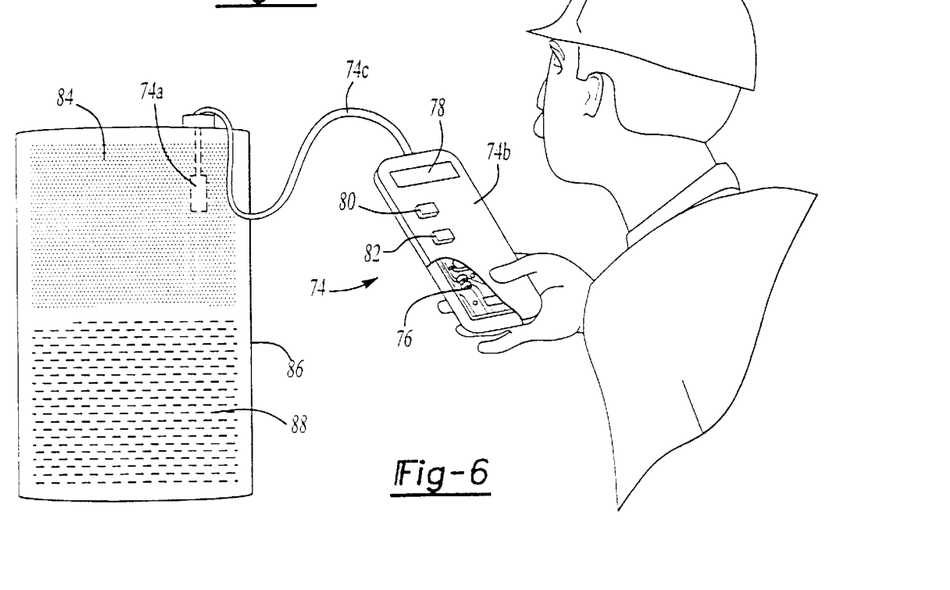
FIG. 6 is an illustration of a person using my galvanic oxygen meter to measure vapor pressure of a volatile fluid in a container.

As to engine control, reid vapor pressure (RVP) is the format that might be desired. As indicated in the steps shown in FIG. 5, RVP can be readily obtained by first obtaining the fuel vapor pressure in metric or other conventional units, and also obtaining the temperature of the vapor. Then, the units are electrically converted to RVP units by a known relationship. The RVP can be displayed on a meter, as shown in FIG.

6, or directly used by an engine control system as indicated by FIG. 4. More specifically, using my galvanic meter, output in mV is directly proportional to oxygen concentration, i.e., pressure. The mathematical relationship between meter output (V) and fuel vapor pressure ($P_g$) is as shown below.

$$V = k\, P_{air} \quad (2)$$

where: V is oxygen meter output in millivolts
  k is an oxygen/nitrogen proportionality constant for air determined from the oxygen meter reading in atmospheric air (20.9% $O_2$ or 14.7 psi air)

$$V_0 = k(14.7) \quad (3)$$

$$V = (V_0/14.7) P_{air} \quad (4)$$

Assuming the fuel, i.e., gasoline, is at atmospheric pressure of 14.7 pounds per square inch, $$P_g = 14.7 - P_{air} \quad (5)$$

Then, from equations (4) and (5), $$P_g = 14.7(1 - V/V_0) \quad (6)$$

The relationship between such measured vapor pressure and reid vapor pressure (RVP) is:

$$\ln P_g = \ln(A*T*RVP) - B/T \quad (7)$$

where: ln is natural logarithm
  RVP is reid vapor pressure
  A is 21.51
  B is 2731.41
  $P_g$ is vapor pressure of fuel in pounds per square inch at the measuring temperature T
  T is the $P_g$ measuring temperature in degrees Kelvin
Solving for RVP:

$$RVP = 1/(A*T) \mathrm{EXP}(\ln P_g + B/T) \quad (8)$$

This conversion in vapor pressure units can be implemented by computer chip calculation or by hard wire electronics and integrated with oxygen meter 32. If my meter is to be used for other purposes, I prefer that oxygen meter 32 take the form of a hand-held meter 74 that includes a sensing tip 74a, a housing portion 74b and interconnecting wires 74c. Sensing tip 74a would include a cathode for exposure to the fuel vapors and a reference anode for comparison. It can include a temperature sensor as well, if desired. The housing portion 74b includes battery-powered electronics 76 for converting oxygen partial pressure readings to vapor pressure units as indicated above. In this hand-held meter, I prefer the units to be kPa or Psi. Housing portion 74b would also include a display 78 to show vapor pressure units. In this example, display 78 is an electronic display, as for example LED, vacuum fluorescent or liquid crystal. Push button 80 would make display 78 show vapor pressure in kPa units. Push button 82 would make the display 78 show vapor pressure in Psi units. My hand-held meter 74 is used by simply inserting sensor tip 74a into the headspace 84 of a tank 86 of fuel or other volatile liquid. While not shown, meter 74 could also have a push button to have the display show reid vapor pressure (RVP). If one is to use a hand-held oxygen meter to determine fuel reid vapor pressure in a bulk storage tank, for example, the scale on the meter might only show RVP units. However, a meter that might show vapor pressure in several different units might be more practical.

Figure 3:
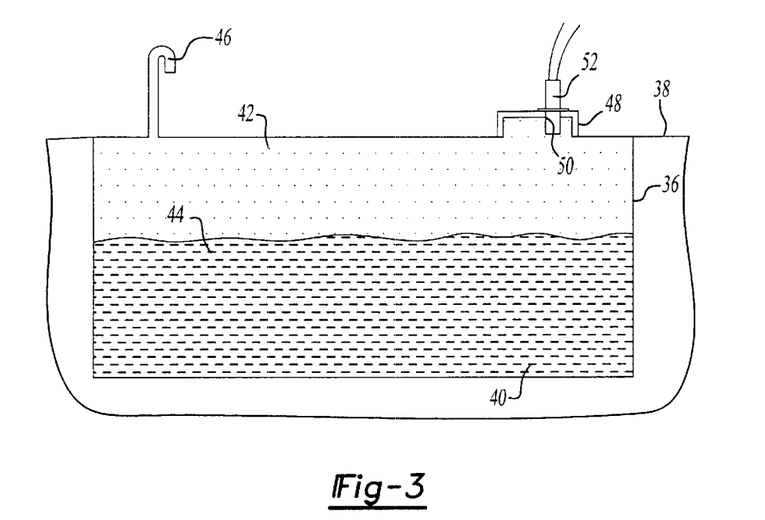
FIG. 3 schematically shows a bulk fuel storage tank whose vapor pressure can be tested in accordance with this invention.

FIG. 3 is included in the drawing hereof to additionally illustrate that this invention is not limited to measuring vapor pressure in an automobile fuel tank or EVAP canister, and not limited to measuring only reid vapor pressure. As indicated above, my meter can be a handy tool for quickly identifying or confirming if a container actually contains the type of fuel, or other volatile liquid, that is supposed to be in that container. My meter can be an especially useful tool for "first cut" identification or confirmation of contents in commercial storage, shipping or transfer containers. In this connection, FIG. 3 shows a bulk fuel storage tank 36 that might be recessed in the surrounding ground 38, as for example at a gasoline service station. Tank 36 is partially filled with fuel 40, which evaporates into the portion 42 of tank 36 above the surface 44 of fuel 40. Portion 42 can be referred to as headspace in tank 36. Tank 36 has an air vent 46 that equilibrates pressure in tank portion 42 to atmospheric pressure. Tank 36 has a fill opening closed by cover 48 that has a threaded smaller opening 50. The sensor tip of an oxygen meter 52 is shown threaded into the smaller opening 50. The sensor tip exposes the cathode (not shown) of the oxygen meter 52 to vapors in the headspace of tank 36. Tank 36 could also be a tank in the hold of a naval tanker ship. Tank 36 need not be recessed as shown. It could be an above-ground storage tank. Tank 36 might also be the tank on a tanker truck, or a tank of any size on any transport means.

The vapor pressure on the fuel inside of tank 36 can be readily measured as indicated above by simply exposing the sensor tip, i.e., the cathode, of the oxygen meter to fuel vapors within tank 36. As indicated above, if the anode of the meter does not have its own source of anode reactant, the anode reference potential can be established by concurrently exposing the anode of the oxygen meter to ambient air. As also indicated above, a comparison of the two electrode potentials provides a ready indication of fuel vapor pressure inside tank 36. In addition, commercial storage, shipping or transfer containers are not always cleansed after being emptied. Residual liquids in them produce a vapor pressure. My oxygen meter can help identify, or confirm, what volatile liquid was previously in the container. Then, a judgment can be better made as to whether the container must be cleansed or not before refilling with a new liquid.

Being able to quickly identify the vapor pressure of the present or prior contents of a tank is a very important diagnostic technique. It can allow one to quickly determine whether a more time-consuming and expensive complete chemical identification of the tank's present or prior contents needs to be made. In instances where purity is of concern and a commercial carrier tank is being re-used, a shipper of a volatile liquid may want to independently confirm what the carrier indicates was last carried in that tank. This is especially true if the tank is large and there are residual liquids still in the tank. A check of vapor pressure of the tank's residual liquids can provide quick "first-cut" independent confirmation as to what the carrier indicated was previously in the tank. Residual liquids might be checkable inside the tank, or a sample portion removed to a special small container adapted to receive the sensor tip of the oxygen meter. Such an independent checking tool can be invaluable to parties employing commercial carriers for shipment of volatile liquids.

Reference is now made to FIG. 4, to briefly describe an EVAP system and its operation. Such a system and its operation are more fully described in my earlier U.S. Pat. No. 5,884,610 Reddy, which is incorporated herein by reference. Some system components shown in FIG. 4 have counterparts shown in FIGS. 1 and 2. The similar counterparts are similarly numbered. FIG. 4 shows a fuel supply tank 10, whose upper interior is in communication with the interior of an EVAP canister 12 by means of vapor line 18 at canister inlet 20. EVAP canister 12 contains activated carbon (not shown) and has ambient air inlet 26 and air valve 28. Air valve 28 might be a normally open, electronically-controlled solenoid valve that is selectively driven to a closed position by controller 54 for diagnostic or maintenance procedures. A fuel vapor outlet of EVAP canister 12 communicates with the air intake 56 of internal combustion engine 14 by means of vapor line 24. Vapor line 24 is normally closed by electronically-controlled solenoid purge valve 34, which opens in response to a signal from controller 54. However, it could be a normally open valve driven closed by the controller 54.

Internal combustion engine 14 receives ambient air through intake air bore 56 which has air intake valve 58 for controlling intake air into intake manifold 60 downstream from air intake valve 58. A conventional pressure transducer 62 provides an intake manifold absolute air pressure (MAP) signal to the controller 54. Engine fuel pump 64 draws fuel from fuel supply tank 10 and provides pressurized fuel to at least one conventional fuel injector 66 which is electronically controlled to meter fuel to engine cylinder intake passages (not shown).

Fuel vapor evaporating from the fuel supply tank 10 and fuel vapor that is displaced from it during refueling operations are trapped for recovery in EVAP canister 12 of the on-board refueling vapor recovery (EVAP) system. When purge valve 34 is driven open by controller 54, EVAP canister 12 is exposed to intake manifold vacuum of a running engine 14. This draws ambient air through the air vent opening 26 of canister 12, across the activated carbon where the ambient air picks up fuel vapor. The fuel vapor-laden air is then drawn through vapor line 24 into the intake manifold 60. In the intake manifold 60, the fuel vapor-laden air is mixed with ambient air from bore 56 and distributed to cylinder intake passages (not shown). Fuel from tank 10 is injected into the air mixture, most often somewhere in the intake manifold 60, for admission to engine cylinders (not shown) and timed combustion therein. A temperature sensor 68 and a mass air flow sensor (not shown) of conventional design may be provided in intake bore 56 to aid in determining the amount of fuel to be injected into the mixture in the intake manifold 60. The temperature sensor provides a MAT output signal to controller 54. The engine cylinder combustion products are exhausted out of engine 14 through exhaust gas conduit 70, in which is disposed at least one zirconia-type exhaust gas sensor 72. Exhaust gas sensor 72 is a conventional wide-range oxygen sensor for transducing oxygen content of the exhaust gas into an output signal (EOS) that can be interpreted by the controller 54.

The descriptions of preferred examples of this invention emphasized measurement of fuel vapor pressures. However, as indicated above, it is believed that this invention has many other uses and applications, and should not be limited except as defined in the appended claims.

What is claimed is:

1. A method of determining vapor pressure of a volatile liquid by galvanically measuring oxygen concentration in a mixture of air and vapors of said liquid, said method comprising the steps of:

exposing a galvanic oxygen meter to a mixture of air and vapors of a volatile liquid, to obtain an electrical output signal from said galvanic oxygen meter based on oxygen partial pressure in said mixture;

comparing said oxygen partial pressure electrical output signal to a reference oxygen partial pressure signal, to obtain an electrical signal indicating a proportion of air remaining in said mixture after displacement of air in said mixture by said vapors; and obtaining an electrical signal representing a proportion of volatile liquid vapor in said mixture as compared to said air proportion by subtracting said air proportion signal from a signal represented by a number one.

2. The method of claim 1 wherein said method further includes displaying said vapor proportion electrical signal as pressure units on a display of said oxygen meter.

3. The method of claim 1 wherein the method further includes converting said vapor proportion into pressure units by a technique selected from the group consisting of:

manually adjusting a variable scale on a display of said oxygen meter to reflect total pressure of said mixture;

multiplying said proportion by measured total pressure of said total mixture; and multiplying said proportion by atmospheric pressure.

4. The method of claim 1 wherein:

said reference oxygen partial pressure is oxygen partial pressure in ambient air at ambient pressure;

said mixture has a total pressure; and said mixture total pressure and pressure of said ambient air are similar.

5. The method of claim 4 wherein:

said mixture and ambient air are at the same temperature; and said mixture total pressure and said ambient air pressure are at atmospheric pressure.

6. The method of claim 4 wherein a constant value is used as reference for said mixture total pressure and said ambient air pressure.

7. A method of measuring vapor pressure of a volatile liquid by galvanically measuring oxygen concentration in a mixture of air and vapors of said liquid, said method comprising the steps of:

exposing a galvanic oxygen meter to a mixture of air and vapors of a liquid whose vapor pressure is to be measured, to thereby obtain an electrical signal from said galvanic oxygen meter based on an oxygen partial pressure in said mixture, said mixture being at a given total pressure;

converting said oxygen partial pressure electrical signal to an electrical signal indicating air partial pressure in said mixture; and obtaining vapor pressure of said volatile liquid by comparing said mixture air partial pressure electrical signal with an electrical signal obtained from similar air at said given total pressure that does not have such fuel vapors.

8. The method of claim 7 wherein:

said mixture oxygen partial pressure electrical signal is obtained by exposing a cathode of said oxygen meter to said mixture at a given temperature;

said air at said given total pressure that does not have such fuel vapors is ambient air;

said given total pressure is ambient air pressure; and said electrical signal obtained from similar air at said given total pressure is an ambient air anode signal obtained by exposing an anode of said oxygen meter to said ambient air.

9. The method of claim 7 wherein:

said electrical signals represent electrode voltages from said oxygen meter; and said comparing to obtain vapor pressure of said volatile liquid is a subtraction of a voltage representing air partial pressure in said mixture from a voltage representing ambient air.

10. The method of claim 7 wherein a similar constant value is used for said given pressure and said ambient pressure.

11. The method of claim 7 wherein:

said ambient air anode signal is obtained while exposing said cathode of said oxygen meter to said mixture; and said ambient air anode signal is used as a reference in converting said oxygen partial pressure to an air pressure signal.

12. The method of claim 11 wherein:

temperature of said mixture is measured at the time oxygen partial pressure of said mixture is measured;

said ambient pressure is measured at the time oxygen partial pressure of said mixture is measured, and vapor pressure units for said volatile liquid are converted to reid vapor pressure units.

13. The method of claim 12 wherein:

said temperature is used to compensate said oxygen partial pressure electrical signal for any differences in measured temperature of said mixture from a reference temperature, to thereby obtain a modified mixture air partial pressure electrical signal for said mixture; and vapor pressure of said volatile liquid is obtained by subtracting said modified air partial pressure signal from an electrical signal representing atmospheric air at said reference temperature.

14. A method of controlling primary fueling of an internal combustion engine in response to measurement of the vapor pressure of fuel vapors in a supplemental air stream drawn into the engine, comprising the steps of:

drawing fuel vapors and atmospheric air into a zone where they form a mixture;

exposing a galvanic oxygen meter to said mixture to thereby obtain a first output voltage from said galvanic oxygen meter based on oxygen partial pressure in the air in said mixture;

applying a pressure proportionality constant for said oxygen meter to said first output voltage to produce a second output voltage that is representative of air partial pressure in said mixture;

subtracting said second output voltage from a reference voltage to produce a signal representative of fuel vapor partial pressure in said mixture;

introducing said mixture in to a n internal combustion engine as a supplemental source of fuel; and while introducing said mixture into said engine, using said signal representative of fuel vapor pressure in said mixture to adjust a primary fuel supply to said engine.

15. The method of claim 14 wherein:

said fuel vapor partial pressure signal is converted to a reid vapor pressure signal; and said primary fuel supply is controlled in response to said reid vapor pressure signal.

16. A meter for galvanically measuring vapor pressure of a volatile liquid, said meter comprising;

an anode for detecting oxygen partial pressure in a mixture of air and vapors of a volatile liquid, said anode providing an anode electrical potential;

a cathode providing a reference electrical potential for comparison with anode electrical potential;

means for measuring the difference in said electrical potentials and for providing said difference as an output signal;

means reacting to said output signal for producing a display signal representing vapor pressure of said volatile liquid; and display means for reacting to said display signal by showing a visible indication of vapor pressure of said volatile liquid.

17. The vapor pressure meter of claim 16 wherein said meter also includes means for converting said display signal into pressure units by a technique selected from the group consisting of:

manually adjusting a variable scale on said display means to reflect vapor pressure of said volatile liquid;

electrically adjusting said output signal to indicate vapor pressure in proportion to atmospheric pressure;

electrically adjusting said output signal to indicate vapor pressure in absolute pressure units; and electrically adjusting said output signal to give any other indication of vapor pressure of said volatile liquid.

* * * * *